(12) United States Patent
Windsor et al.

(10) Patent No.: US 11,666,185 B1
(45) Date of Patent: Jun. 6, 2023

(54) PORTABLE HAND-WASHING KIT

(71) Applicants: Travis Windsor, Bethany (CA); Jodi Windsor, Bethany (CA)

(72) Inventors: Travis Windsor, Bethany (CA); Jodi Windsor, Bethany (CA)

( * ) Notice: Subject to any disclaimer, the term of this patent is extended or adjusted under 35 U.S.C. 154(b) by 330 days.

(21) Appl. No.: 17/080,965

(22) Filed: Oct. 27, 2020

(51) Int. Cl.
| | | |
|---|---|---|
| A47K 7/00 | (2006.01) | |
| A01N 25/02 | (2006.01) | |
| A47K 1/00 | (2006.01) | |
| A01N 25/34 | (2006.01) | |
| A01N 43/66 | (2006.01) | |
| A01N 59/12 | (2006.01) | |
| A01N 43/36 | (2006.01) | |
| A01N 33/12 | (2006.01) | |
| A01N 47/30 | (2006.01) | |

(52) U.S. Cl.
CPC ............... *A47K 7/00* (2013.01); *A01N 25/02* (2013.01); *A01N 25/34* (2013.01); *A01N 33/12* (2013.01); *A01N 43/36* (2013.01); *A01N 43/66* (2013.01); *A01N 47/30* (2013.01); *A01N 59/12* (2013.01); *A47K 1/00* (2013.01)

(58) Field of Classification Search
CPC .............. A47K 1/00; A47K 7/00; A61H 35/00
USPC ........................................................... 4/619
See application file for complete search history.

(56) References Cited

U.S. PATENT DOCUMENTS

| | | | |
|---|---|---|---|
| 3,263,653 A | 8/1966 | Miller | |
| 3,699,984 A | 10/1972 | Davis | |
| 3,757,806 A | 9/1973 | Bhaskar | |
| 4,083,328 A | 4/1978 | Baker | |
| 4,465,522 A | 8/1984 | Taldo | |
| 5,241,953 A | 9/1993 | Sykes | |
| 5,279,257 A | 1/1994 | Temby | |
| 5,522,411 A * | 6/1996 | Johnson | A47K 10/48 134/107 |
| 6,161,227 A * | 12/2000 | Bargenquast | A47K 5/1217 134/58 R |
| 6,695,800 B1 * | 2/2004 | Gary | A61H 35/00 132/74.5 |
| 9,585,522 B1 * | 3/2017 | Brown, Sr. | B60R 9/02 |
| 2006/0070179 A1 * | 4/2006 | Siegal | A61H 35/006 4/622 |
| 2011/0301459 A1 | 12/2011 | Gharib | |
| 2016/0100551 A1 | 4/2016 | Hanneken | |

FOREIGN PATENT DOCUMENTS

CA             1206067       6/1986

\* cited by examiner

*Primary Examiner* — Huyen D Le
(74) *Attorney, Agent, or Firm* — Kyle A. Fletcher, Esq.

(57) ABSTRACT

The portable hand-washing kit is a kit. The portable hand-washing kit is adapted for use with a patient. The portable hand-washing kit is a portable structure that allows the patient to wash their hands. The portable hand-washing kit comprises a disinfecting structure, a disinfecting compound, and water. The disinfecting compound is contained in the disinfecting structure. The water is added to the disinfecting structure before the use of the portable hand-washing kit by the patient. The patient washes their hands by inserts their hands into the solution formed by dissolving the disinfecting compound in the water. The disinfecting compound is pharmacologically active media that poisons the biochemical processes of microorganisms including viruses such as COVID-19.

19 Claims, 7 Drawing Sheets

I-I

CAS 25655-41-8

CAS 8001-54-5

CAS 3880-34-5

CAS 101-20-2

CAS 2893-78-9

PORTABLE HAND-WASHING KIT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science, more specifically, an apparatus using chemical means for disinfecting objects other than foodstuffs or contact lenses. (A62L2/16)

Biological Background

A virus is a microorganism. A virus comprises a nucleic acid and a protein shell. The protein shell forms a containment structure for the nucleic acid structure. In this disclosure, the virus is assumed to be a poison or, more specifically a toxin. The terms poison and toxin are defined elsewhere in this disclosure. The virus is a biochemical structure that "infects" a host cell. By infecting a host cell is meant that the virus deposits the nucleic acid structure in the host cell such that the energy produced by the biochemical processes within the host cell is diverted towards the replication of the nucleic acid structure of the virus. An evolved virus refers to a virus that further comprises an envelope. The envelope is a lipid based structure that is similar to a cell membrane. The envelope encloses and protects the nucleic acid structure and the protein shell. The virus is defined elsewhere in this disclosure.

SUMMARY OF INVENTION

The portable hand-washing kit is a kit. The portable hand-washing kit is adapted for use with a patient. The portable hand-washing kit is a portable structure that allows the patient to wash their hands. The portable hand-washing kit comprises a disinfecting structure, a disinfecting compound, and water. The disinfecting compound is contained in the disinfecting structure. The water is added to the disinfecting structure before the use of the portable hand-washing kit by the patient. The patient washes their hands by inserts their hands into the solution formed by dissolving the disinfecting compound in the water. The disinfecting compound is pharmacologically active media that poisons the biochemical processes of microorganisms including viruses such as COVID-19.

These together with additional objects, features and advantages of the portable hand-washing kit will be readily apparent to those of ordinary skill in the art upon reading the following detailed description of the presently preferred, but nonetheless illustrative, embodiments when taken in conjunction with the accompanying drawings.

In this respect, before explaining the current embodiments of the portable hand-washing kit in detail, it is to be understood that the portable hand-washing kit is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the portable hand-washing kit.

It is therefore important that the claims be regarded as including such equivalent construction insofar as they do not depart from the spirit and scope of the portable hand-washing kit. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
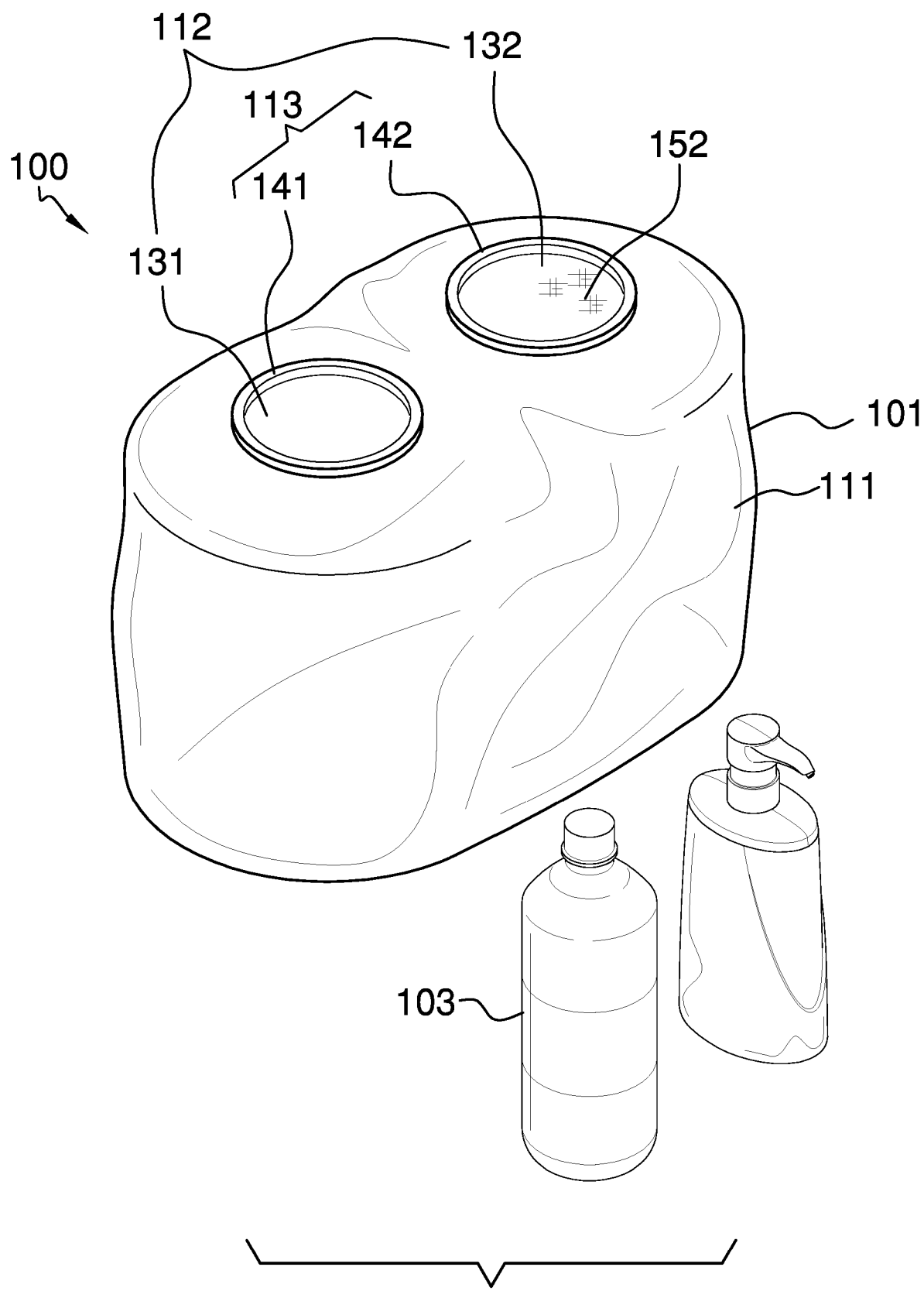
FIG. 1 is a kit view of an embodiment of the disclosure.
Figure 2:
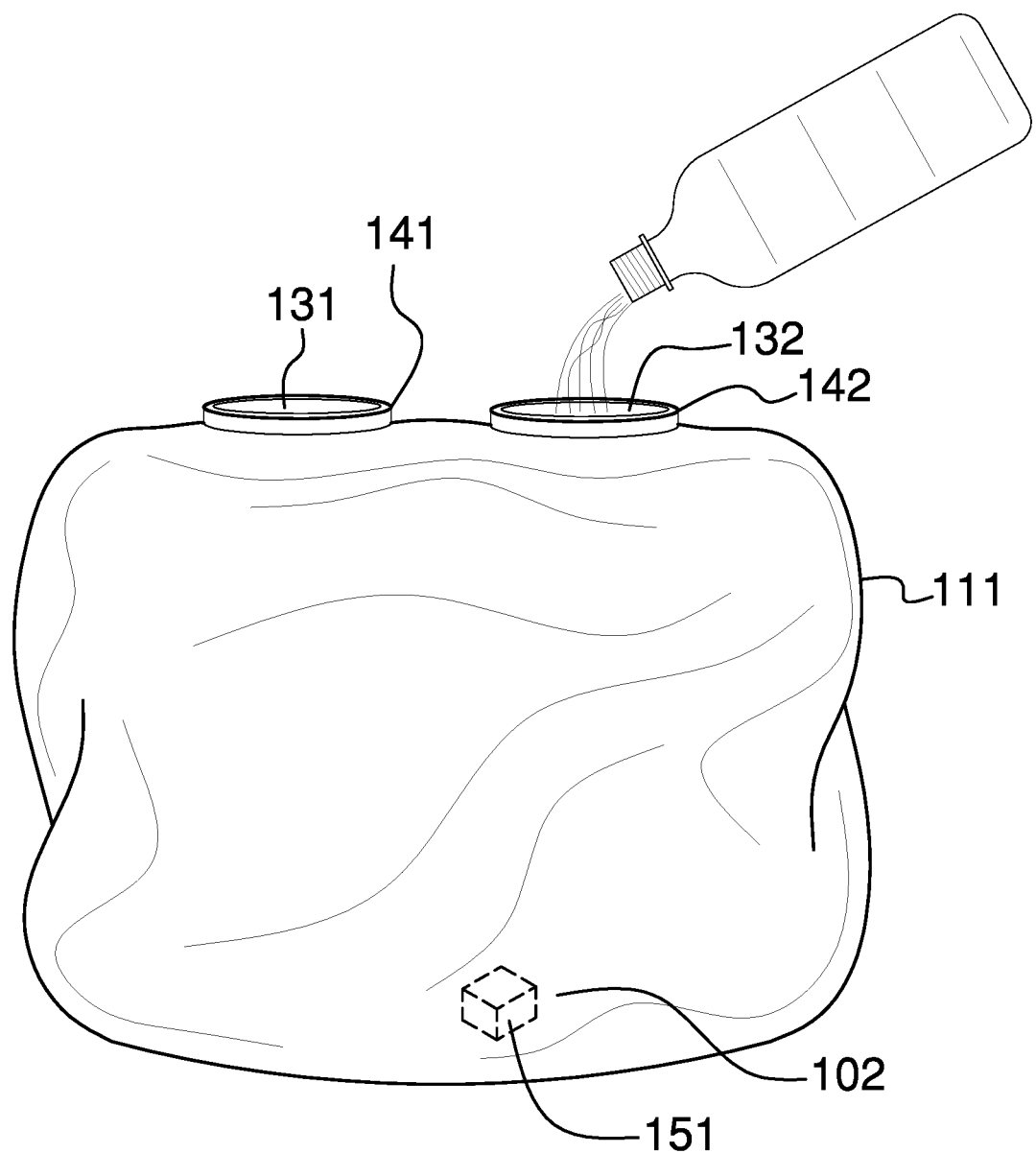
FIG. 2 is a front view of an embodiment of the disclosure.
Figure 3:
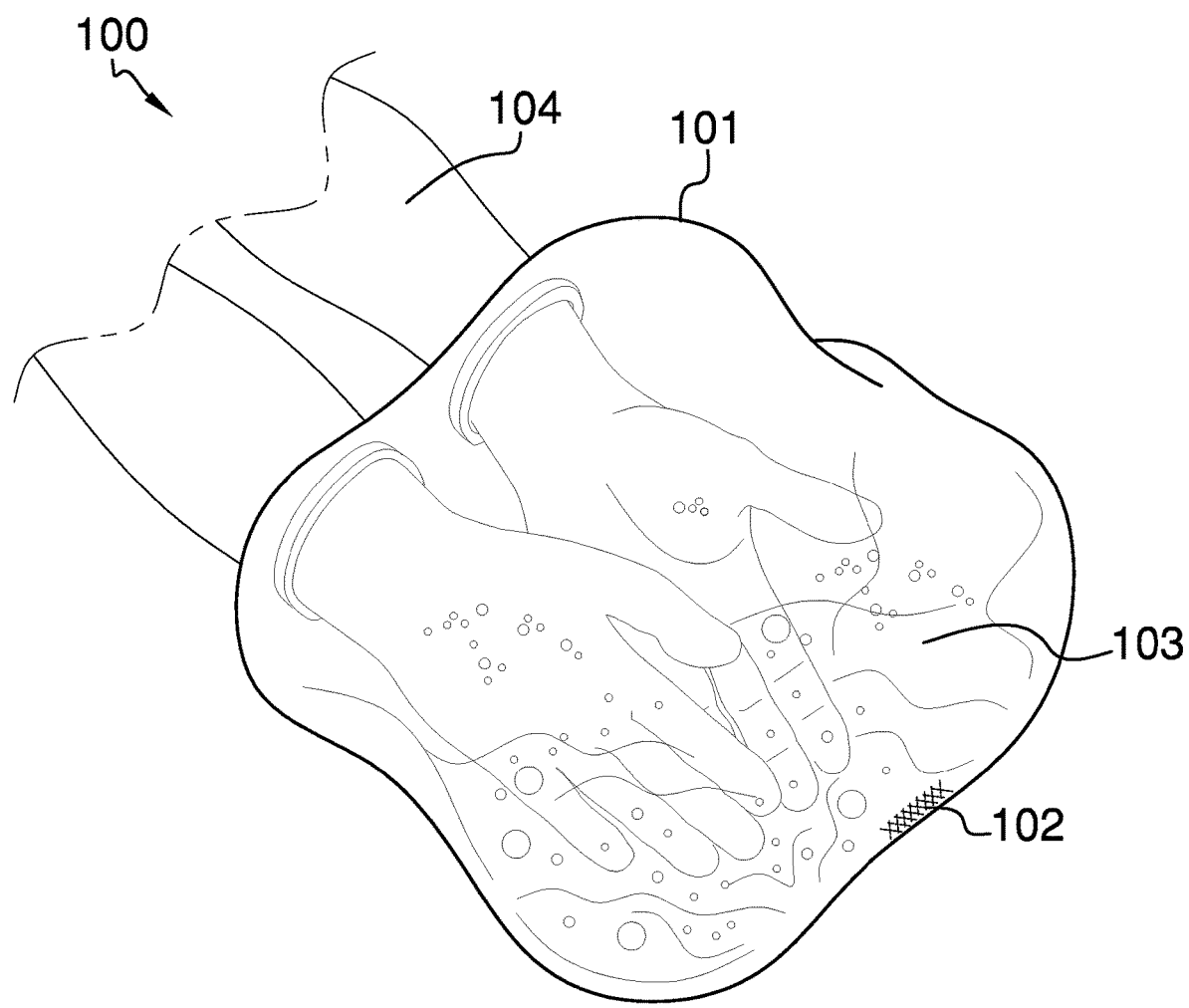
FIG. 3 is an in-use view of an embodiment of the disclosure.
Figure 4:
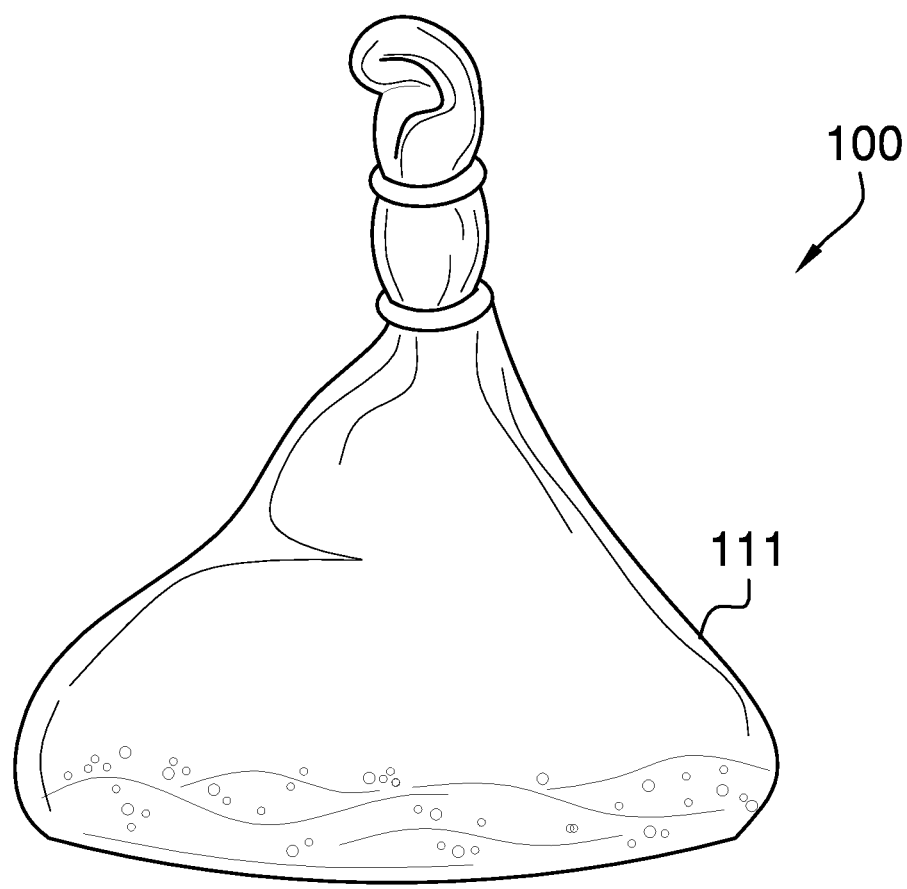
FIG. 4 is an in-use view of an embodiment of the disclosure.
Figure 5:
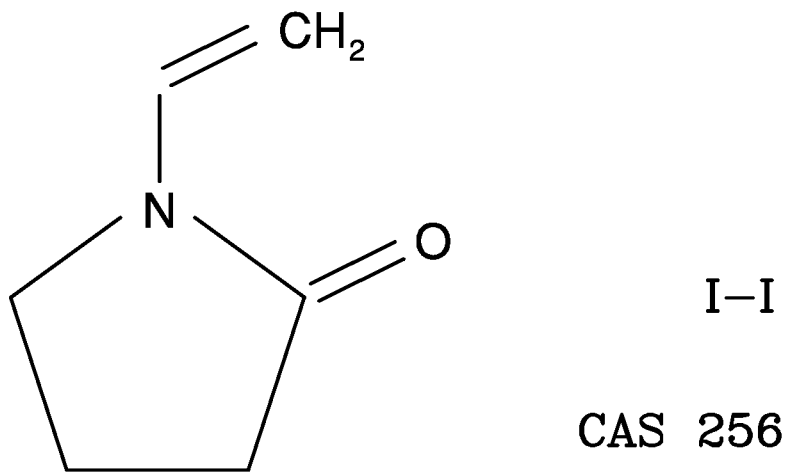
FIG. 5 is a detail view of an embodiment of the disclosure.
Figure 6:
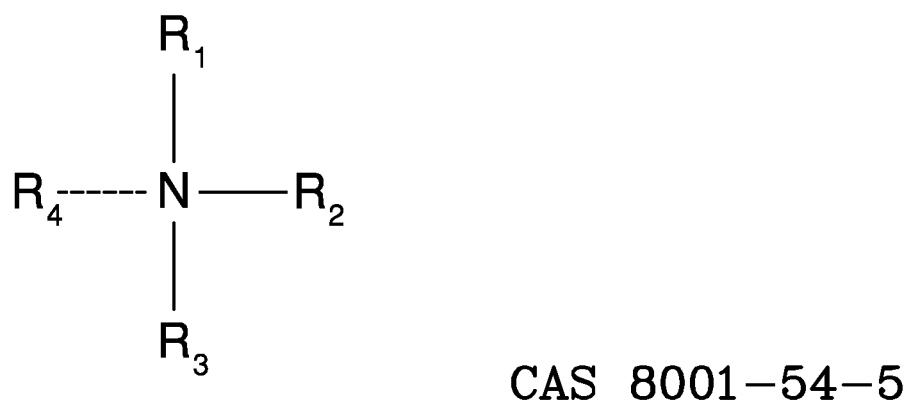
FIG. 6 is a detail view of an embodiment of the disclosure.
Figure 7:
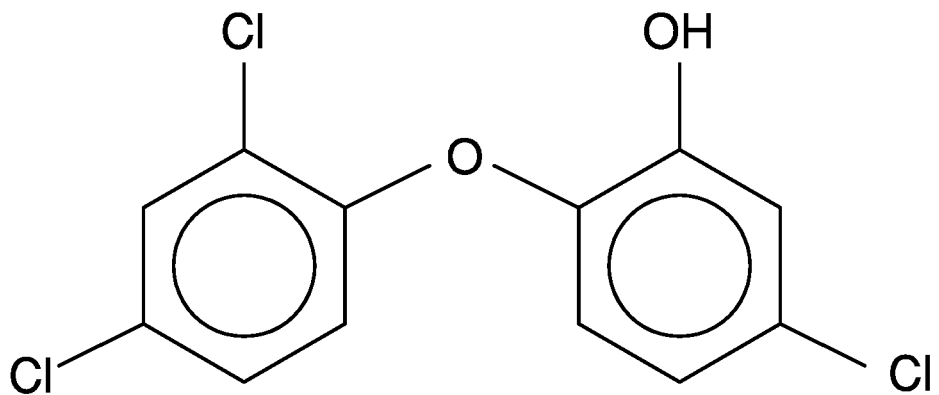
FIG. 7 is a detail view of an embodiment of the disclosure.
Figure 8:
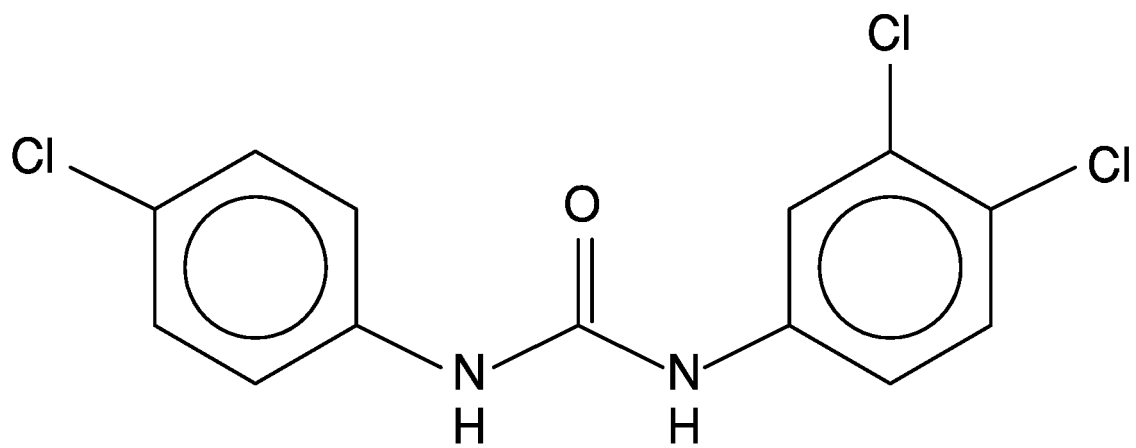
FIG. 8 is a detail view of an embodiment of the disclosure.
Figure 9:
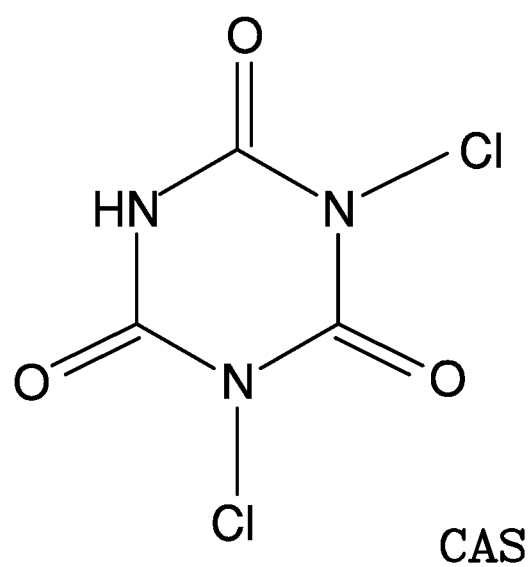
FIG. 9 is a detail view of an embodiment of the disclosure.

Detailed reference will now be made to one or more potential embodiments of the disclosure, which are illustrated in FIGS. 1 through 9.

The portable hand-washing kit 100 (hereinafter invention) is a kit. The invention 100 is adapted for use with a patient 104. The invention 100 is a portable structure that allows the patient 104 to wash their hands. The invention 100 comprises a disinfecting structure 101, a disinfecting compound 102, and water 103. The disinfecting compound 102 is contained in the disinfecting structure 101. The water 103 is added to the disinfecting structure 101 before the use of the invention 100 by the patient 104. The patient 104 washes their hands by inserts their hands into the solution formed by dissolving the disinfecting compound 102 in the water 103. The disinfecting compound 102 is pharmacologically active media that poisons the biochemical processes of microorganisms including viruses such as COVID-19.

The water 103 is defined elsewhere in this disclosure. The water 103 forms the solvent used to dissolve the disinfecting compound 102.

The disinfecting structure 101 is a container. The disinfecting structure 101 is a flexible structure. The disinfecting structure 101 has an inelastic nature. The disinfecting structure 101 is a fluid impermeable structure. The disinfecting structure 101 is a self-standing structure. The disinfecting structure 101 is a disposable structure. The disinfecting structure 101 contains the disinfecting compound 102 when the invention 100 is stored in anticipation of subsequent use. The disinfecting structure 101 contains a disinfecting solution after the water 103 has been poured into the disinfecting structure 101. The disinfecting solution contained in the disinfecting structure 101 is used to wash the hands of the patient 104.

The disinfecting structure 101 is intended for a single use. The flexible structure of the disinfecting structure 101 allows the disinfecting structure 101 to twist into a closed position.

The disinfecting structure 101 comprises a containment structure 111, a plurality of access apertures 112, and a plurality of elastic bands 113.

The containment structure 111 forms the containment vessel that holds the disinfecting solution formed by the disinfecting compound 102 and the water 103. The containment structure 111 is formed from a sheeting. The containment structure 111 is formed as a bag. In the first potential embodiment of the disclosure, the sheeting that forms the containment structure 111 is formed from a polyurethane. The containment structure 111 is formed as a flexible structure that is capable of being twisted into a closed position. The containment structure 111 is formed with enough stiffness that the containment structure 111 forms a self-standing while a patient 104 is washing their hands.

Each of the plurality of access apertures 112 is an aperture that is formed through the exterior surface of the containment structure 111. A hand of the patient 104 inserts into the containment structure 111 through an access aperture selected from the plurality of access apertures 112. The plurality of access apertures 112 comprises a first access aperture 131 and a second access aperture 132.

The first access aperture 131 is an aperture formed through the containment structure 111. The first access aperture 131 forms an access port into the interior of the containment structure 111. A first hand of the patient 104 inserts into the first access aperture 131 of the containment structure 111.

The second access aperture 132 is an aperture formed through the containment structure 111. The second access aperture 132 forms an access port into the interior of the containment structure 111. A second hand of the patient 104 inserts into the second access aperture 132 of the containment structure 111.

Each of the plurality of elastic bands 113 is an elastic structure that attaches to an access port selected from the plurality of access apertures 112. Each of the plurality of access apertures 112 secures its associated access port to the hand of the patient 104. The plurality of access apertures 112 comprises a first elastic band 141 and a second elastic band 142.

The first elastic band 141 is an elastic structure. The first elastic band 141 is a band that attaches to the perimeter of the first access aperture 131. The first elastic band 141 seals the first access aperture 131 around the hand of the patient 104 when it is inserted into the containment structure 111.

The first elastic band 141 acts as a spring. Specifically, when a first hand of the patient 104 inserts into the first elastic band 141, the pressing of the first hand of the patient 104 against the first elastic band 141 applies a force that displaces the first elastic band 141 in a direction that is perpendicular to the center axis of the first elastic band 141. The elasticity of the first elastic band 141 creates a force that opposes the displacement created by the insertion of the first hand of the patient 104 into the first elastic band 141. This opposing force is in a direction that returns the first elastic band 141 to its relaxed shape. Because the first hand of the patient 104 prevents the first elastic band 141 from returning completely to its relaxed shape, the first elastic band 141 applies a force against the first hand of the patient 104 that holds the first elastic band 141 in position.

The second elastic band 142 is an elastic structure. The second elastic band 142 is a band that attaches to the perimeter of the second access aperture 132. The second elastic band 142 seals the second access aperture 132 around the hand of the patient 104 when it is inserted into the containment structure 111.

The second elastic band 142 acts as a spring. Specifically, when a second hand of the patient 104 inserts into the second elastic band 142, the pressing of the second hand of the patient 104 against the second elastic band 142 applies a force that displaces the second elastic band 142 in a direction that is perpendicular to the center axis of the second elastic band 142. The elasticity of the second elastic band 142 creates a force that opposes the displacement created by the insertion of the second hand of the patient 104 into the second elastic band 142. This opposing force is in a direction that returns the second elastic band 142 to its relaxed shape. Because the second hand of the patient 104 prevents the second elastic band 142 from returning completely to its relaxed shape, the second elastic band 142 applies a force against the second hand of the patient 104 that holds the second elastic band 142 in position.

The disinfecting compound 102 is a chemical compound. The disinfecting compound 102 is a pharmacologically active media. The disinfecting compound 102 forms a poison that disrupts the biochemical processes of a microorganism including viruses such as COVID-19. The disinfecting compound 102 dissolves to form a disinfecting solution when the water 103 is added to the disinfecting structure 101. The disinfecting solution formed by the disinfecting compound 102 is used to wash the hands of the patient 104.

The disinfecting compound 102 has a structure selected from the group consisting of a tablet structure 151 and a surface coating 152. The tablet structure 151 is a compressed structure formed from the disinfecting compound 102. The tablet structure 151 is stored within the containment structure 111. The surface coating 152 is a coating formed by the disinfecting compound 102. The surface coating 152 is applied to the interior surfaces of the containment structure 111.

The disinfecting compound 102 is a chemical compound selected from the group consisting of: a) 2-pyrrolidinone with iodine (CAS 25655-41-8); b) a mixture of 5-chloro-2-

(2,4-dichlorophenoxy)-phenol (CAS 3380-34-5) and sodium bicarbonate (CAS 144-55-8); c) a mixture of N-(4-chlorophenyl)-N'-(3,4-dichlorophenyl)-urea (CAS 101-20-2) and sodium bicarbonate (CAS 144-55-8); d) a quaternary ammonium (CAS 8001-54-5), and, e) a sodium 3,5-dichloro-2,4,6-trioxy,1,3,5-triazinan-1-ide (CAS 2893-78-9).

The 2-pyrrolidinone with iodine (CAS 25655-41-8) is a pharmacologically active media. The 2-pyrrolidinone with iodine (CAS 25655-41-8) is a topically applied disinfectant. The 2-pyrrolidinone with iodine (CAS 25655-41-8) is listed as an antiseptic in the World Health Organization List of Essential Medicines.

The 5-chloro-2-(2,4-dichlorophenoxy)-phenol (CAS 3380-34-5) is a pharmacologically active media. The 5-chloro-2-(2,4-dichlorophenoxy)-phenol (CAS 3380-34-5) is a topically applied antimicrobial compound. The 5-chloro-2-(2,4-dichlorophenoxy)-phenol (CAS 3380-34-5) is provisioned as a mixture of 5-chloro-2-(2,4-dichlorophenoxy)-phenol (CAS 3380-34-5) and sodium bicarbonate (CAS 144-55-8). The sodium bicarbonate (CAS 144 8) is added to improve the solubility of the 5-chloro-2-(2,4-dichlorophenoxy)-phenol (CAS 3380-34-5) of the water 103.

The N-(4-chlorophenyl)-N'-(3,4-dichlorophenyl)-urea (CAS 101-20-2) is a pharmacologically active media. The N-(4-chlorophenyl)-N'-(3,4-dichlorophenyl)-urea (CAS 101-20-2) is a topically applied antimicrobial compound. The N-(4-chlorophenyl)-N'-(3,4-dichlorophenyl)-urea (CAS 101-20-2) is provisioned as a mixture of N-(4-chlorophenyl)-N'-(3,4-dichlorophenyl)-urea (CAS 101-20-2) and sodium bicarbonate (CAS 144-55-8). The sodium bicarbonate (CAS 144-55-8) is added to improve the solubility of the N-(4-chlorophenyl)-N'-(3,4-dichlorophenyl)-urea (CAS 101-20-2) of the water 103.

The quaternary ammonium (CAS 8001-54-5) is a pharmacologically active media. The quaternary ammonium (CAS 8001-54-5) is a topically applied antimicrobial compound.

The sodium 3,5-dichloro-2,4,6-trioxy,1,3,5-triazinan-1-ide (CAS 2893-78-9) is a pharmacologically active media. The sodium 3,5-dichloro-2,4,6-trioxy,1,3,5-triazinan-1-ide (CAS 2893-78-9) is a topically applied antimicrobial compound.

In the first potential embodiment of the disclosure, the intent of the applicant is to protect that patient 104 against a virus such as the COVID-19 virus. A virus is a microorganism. A virus comprises a nucleic acid and a protein shell. The protein shell forms a vessel for the nucleic acid structure. In this disclosure, the virus is assumed to be a poison or, more specifically a toxin. The terms poison and toxin are described elsewhere in this disclosure. The virus is a biochemical structure that "infects" a host cell. By infecting a host cell is meant that the virus deposits the nucleic acid structure in the host cell such that the energy produced by the biochemical processes within the host cell is diverted towards the replication of the nucleic acid structure of the virus. An evolved virus refers to a virus that further comprises an envelope. The envelope is a lipid based structure that is similar to a cell membrane. The envelope encloses and protects the nucleic acid structure and the protein shell. The virus is defined elsewhere in this disclosure. The COVID-19 virus is defined in elsewhere in this disclosure.

The following definitions were used in this disclosure:

2-pyrrolidinone with iodine: As used in this disclosure, 2-pyrrolidinone with iodine (CAS 25655-41-8) is a topical disinfectant chemical substance commonly referred to as povidone-iodine.

5-chloro-2-(2,4-dichlorophenoxy)-phenol: As used in this disclosure, 5-chloro-2-(2,4-dichlorophenoxy)-phenol (CAS 3380-34-5) is an antifungal and antibiotic agent that is commonly used in consumer products. 5-chloro-2-(2,4-dichlorophenoxy)-phenol is commonly referred to as triclosan.

Amino Acid: As used in this disclosure, an amino acid refers to a carbon atom that has a carboxyl functional group and an amine functional group. The standard amino acids refers to the twenty to twenty two-amino acids commonly used for biological functions. The range of twenty to twenty two depends on the specific context: the first twenty amino acids refer to the amino acids that are incorporated into proteins using the normal biosynthetic process while two additional amino acids can be incorporated into proteins using alternate biological mechanisms.

Ammonia: As used in this disclosure, ammonia (CAS 7664-41-7) refers to a chemical compound with the formula NH3. The chemical term ammonium (CAS 14789-03-9) refers to an ammonia molecule that has formed a hydrogen bond with a hydrogen ion. Ammonium has the chemical formula NH4+. The chemical quaternary ammonium (CAS 8001-54-5) refers to a chemical compound wherein the hydrogen elements of ammonium, including the hydrogen bonded hydrogen ion are replaced with other molecules or atoms (potentially including hydrogen). The US EPA considers quaternary ammonium to be effective against SARs-like viruses including COVID-19.

Aperture: As used in this disclosure, an aperture is a prism-shaped negative space that is formed completely through a structure or the surface of a hollow structure.

Bag: As used in this disclosure, a bag is a container made of a flexible material. The bag has a single opening which allows the bag to receive the items to be contained.

Band: As used in this disclosure, a band is a flat loop of material.

Bicarbonate: As used in this disclosure, bicarbonate (CAS 71-52-3) refers to the anionic molecule with a formula HCO3-. Common molecular structures containing bicarbonate include, but are not limited carbonic acid (CAS 463-79-6 Formula CH2O3) and sodium bicarbonate (CAS 144-55-8 Formula NaHCO3).

Biochemistry: As used in this disclosure, biochemistry refers to the chemical substances and the chemical processes associated with biological processes.

Carbamate: As used in this disclosure, a carbamate is a functional group consisting of an O—(C═O)—N structure. Carbamate is informally referred to as urethane.

Carboxylic Acid: As used in this disclosure, a carboxylic acid is an organic molecule that further comprises the carboxyl functional group.

Carboxyl Functional Group: As used in this disclosure, the carboxyl functional group is a functional group with the chemical formula —COOH.

Coating: As used in this disclosure, a coating refers to a substance that is applied to the exterior surface of an object such that the coating forms a new exterior surface of the object. A coating is commonly said to be formed as a layer. Paint is an example of a common coating material.

Container: As used in this disclosure, a container is a structure that forms a protected space used to store and transport an object.

Copolymer: As used in this disclosure, a copolymer is a polymer formed from two or more repeating molecules (also referred to as monomers).

COVID-19: As used in this disclosure, COVID-19 is a virus that is highly contagious between humans. The COVID-19 virus is also known as the severe acute respiratory syndrome coronavirus 2 (SARS-CoV-2). The COVID-19 is responsible for the COVID-19 pandemic of 2020. The COVID-19 is an evolved virus. The COVID-19 has a diameter a range of between 50 and 200 nanometers. This disclosure assumes that a representative diameter for COVID-19 is 100 nanometers. As of the writing of this definition, the environmental stability (the half-life survival time of the virus outside of the host) is between one and ten hours.

Disinfectant: As used in this disclosure, a disinfectant is a chemical that destroys or inhibits the activities of pathogenic microorganisms.

Disposable: As used in this disclosure, disposable is an adjective that refers to an object that is designed and intended for a single use. Within this context, an object would be considered disposable if it is not reusable after its initial use.

Dissolve: As used in this disclosure, to dissolve refers to the incorporation of a solute into a solvent to form a solution.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Band: As used in this disclosure, an elastic band is a loop of textile that is formed using elastic material that can stretched. Alternatively, the elastic band can be a sheeting that is formed from latex, spandex, or an elastic plastic film that can be stretched.

Elastic Nature: As used in this disclosure, an elastic nature refers to a flexible structure that returns to its relaxed shape after the flexible structure has been deformed.

Fatty Acid: As used in this disclosure, a fatty acid refers to a carboxylic acid with a continuous carbon chain of greater than 3 carbon atoms beyond the carboxyl functional group.

Flexible: As used in this disclosure, flexible refers to an object or material that will deform when a force is applied to it but that will not necessarily return to its original shape when the deforming force is removed.

Fluid: As used in this disclosure, a fluid refers to a state of matter wherein the matter is capable of flow and takes the shape of a container it is placed within. The term fluid commonly refers to a liquid or a gas.

Functional Group: As used in this disclosure, a functional group is specific chemical structure that 1) defines the structure of a chemical family; and, 2) determines the properties of the chemical family. Common functional groups include, but are not limited to, aldehydes, alkanes, alkenes, alkynes, alcohols, amides, amines, carboxylic acids, esters, ethers, haloalkanes, haloalkenes, haloalkynes, and ketones. As a practical matter, the intention of this definition is to use the term functional group in the same manner as the term is commonly used in organic chemistry.

Gas: As used in this disclosure, a gas refers to a state (phase) of matter that is fluid and that fills the volume of the structure that contains it. Stated differently, the volume of a gas always equals the volume of its container.

Inelastic Nature: As used in this disclosure, an inelastic nature refers to a flexible structure that maintains its new shape after the flexible structure has been deformed.

Kit: As used in this disclosure, a kit is an assembly of a combination of instruments, equipment, or supplies that are dedicated or intended for use in a specific purpose. Depending on the context, a kit may further include the container within which the instruments, equipment, and supplies are stored.

Lipid: As used in this disclosure, a lipid is an organic molecule that is soluble in nonpolar solvents.

Liquid: As used in this disclosure, a liquid refers to a state (phase) of matter that is fluid and that maintains, for a given pressure, a fixed volume that is independent of the volume of the container.

Loop: As used in this disclosure, a loop is the length of a first linear structure including, but not limited to, shafts, lines, cords, or webbings, that is: 1) folded over and joined at the ends forming an enclosed space; or, 2) curved to form a closed or nearly closed space within the first linear structure. In both cases, the space formed within the first linear structure is such that a second linear structure such as a line, cord or a hook can be inserted through the space formed within the first linear structure. Within this disclosure, the first linear structure is said to be looped around the second linear structure.

Microorganism: As used in this disclosure, a microorganism is an organism too small to be viewed by the unaided eye. Microorganisms are typically single celled organisms such as bacteria, yeast, viruses, protozoa, fungi and algae. A pathogen refers to a microorganism that has the potential to cause illness or disease.

Monomer: As used in this disclosure, a monomer refers to a molecular structure that bonds to itself in a repeating manner to form a polymer.

N-(4-chlorophenyl)-N'-(3,4-dichlorophenyl)-urea: As used in this disclosure, N-(4-chlorophenyl)-N'-(3,4-dichlorophenyl)-urea (CAS 101-20-2) is an antibacterial agent commonly found in soaps. N-(4-chlorophenyl)-N'-(3,4-dichlorophenyl)-urea is commonly called triclocarban.

Non-Polar Molecule: As used in this disclosure, a non-polar molecule refers to a molecular structure that: a) is electrically neutral; and, b) has a uniform spatial distribution of the electrons within the molecule.

Organic: As used in this disclosure, organic refers to a carbon-based chemical structure. A limited number of (mostly) carbon-based salts are traditionally considered inorganic chemical structures and are excluded from the study of organic chemistry.

Patient: As used in this disclosure, a patient is a person who is designated to receive a medical treatment, therapy or service. The term patient may be extended to an animal when used within the context of the animal receiving veterinary treatment or services.

Pharmacologically Active Media: As used in this disclosure, a pharmacologically active media refers to a chemical substance that has a biochemical or physiological effect on a biological organism.

Phase: As used in this disclosure, phase refers to the state of the form of matter. The common states of matter are solid, liquid, gas, and plasma.

Plasma: As used in this disclosure, plasma refers to a state (phase) of matter wherein the outer valence electrons of an atom (or molecule) have been separated from their nucleus but remain with the matter. A plasma is an electrically neutral state of matter that is formed from the ions of the separated atoms. Plasmas generally, but not necessarily behaves like a gas in that a plasma fills the volume of the structure that contains it.

Poison: As used in this disclosure, a poison is a chemical substance that interferes with the normal biological processes of a biological organism. The term poison often implies the injury to or death of the biological organism. A toxin is a poison that generates an immune system response.

Polar Molecule: As used in this disclosure, a polar molecule refers to a molecular structure that: a) is electrically neutral; but, b) does not have a uniform spatial distribution of the electrons within the molecule. A polar molecule will present one or more electrically positive poles and the same number of electrically negative poles within the molecular structure.

Polarity: As used in this disclosure, the term polarity is used to describe a physical property or physical characteristic wherein: 1) the physical property or physical characteristic manifests two opposing attributes, tendencies, characteristics, or principals; and, 2) the two opposing attributes, tendencies, characteristics, or principals have an intrinsic separation, alignment, or orientation.

Polymer: As used in this disclosure, a polymer refers to a molecular chain that comprises multiple repeating units known as monomers. The repeating unit may be an atom or a molecular structure.

Polyurethane: As used in this disclosure, a polyurethane is a copolymer wherein the one or more monomer chains are linked together carbamates.

Portable: As used in this disclosure, the term portable refers to an object with a form factor and weight that allows an individual to physically carry the object to its intended destination.

Primary Chemical Structure: As used in this disclosure, a primary chemical structure refers to a family of chemical structures that: a) share a common chemical structure; and that, b) are differentiated by differences in the one or more functional that are attached to the primary chemical structure.

Protected Space: As used in this disclosure, a protected space is a negative space within which an object is stored. The protected space is enclosed by a boundary structure, often referred to as a guard, that prevents impacts from damaging the object contained within the protected space.

Protein: As used in this disclosure, a protein refers to a molecular sequence of amino acids. Unless otherwise stated in this disclosure, a protein is exclusively formed from the standard amino acids. The order of the standard amino acids within the protein is said to be the primary structure of the protein. A protein that is formed from biological mechanisms is formed with a series of secondary, tertiary, and quaternary bonds that form the secondary, tertiary, and quaternary structure that form the characteristic shape of the specific protein. A protein that has had one or more of the secondary, tertiary, and quaternary bonds broken is said to be denatured.

Relaxed Shape: As used in this disclosure, a structure is considered to be in its relaxed state when no shear, strain, or torsional forces are being applied to the structure.

Rotation: As used in this disclosure, rotation refers to the cyclic movement of an object around a fixed point or fixed axis. The verb of rotation is to rotate.

Salt: As used in this disclosure, a salt means an ionic compound that further comprises at least one atom of a metallic element or compound and one atom of a non-metallic element or compound. When dissolved in water, the ionic compound releases the metallic element and the non-metallic element into the water as ions. In this disclosure, a metallic element is assumed to include the alkali metals and the alkali earth metals. Alternatively, and equivalently, a metallic element may be assumed to be any element on the periodic table that is to the left of the metalloids.

Self-Standing: As used in this disclosure, self-standing refers to a mechanical structure that: a) remains stable on a supporting surface; without, b) requiring the transfer of a portion of the load of the mechanical structure to load paths provided by structures that are independent of the mechanical structure.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Soap: As used in this disclosure, a soap is a cleansing chemical that is used in cleaning an object. A soap is generally formed from a mixture of one or more salts and one or more fatty acids.

Sodium Dichloroisocyanurate: As used in this disclosure, sodium dichloroisocyanurate is a commonly used name for sodium 3,5-dichloro-2,4,6-trioxy,1,3,5-triazinan-1-ide (CAS 2893-78-9). Sodium dichloroisocyanurate is a commonly used disinfecting agent that is available in a powder form. Sodium dichloroisocyanurate is soluble in water and alcohol. Sodium dichloroisocyanurate is also available in a dihydride formulation (sodium dichloroisocyanurate hydride CAS: 51580 0). Sodium dichloroisocyanurate is soluble in water at concentrations of over 200 grams per liter.

Solid: As used in this disclosure, a solid refers to a state (phase) of matter that: 1) has a fixed volume; and, 2) does not flow.

Solution: As used in this disclosure, a solution is a uniform mixture of two or more compounds in a liquid phase. The major component selected from the two or more compounds that forms the solution is called the solvent. The components remaining in the two or more compounds are called the solute. A polar solvent is a solvent formed from polar molecules. A non-polar solvent is a solvent formed from non-polar molecules. The rule of thumb that "like dissolves like" states that: a) solutes formed from polar molecules will dissolve in polar solvents but will not dissolve in non-polar solvents; and, b) solutes formed from non-polar molecules will dissolve in non-polar solvents but will not dissolve in polar solvents.

Surfactant: As used in this disclosure, a surfactant is a substance that decreases the surface tension of a fluid. Within water, a surfactant often comprises polar and non-polar functional groups for the purpose of improving the solubility of otherwise non-soluble substances in water.

Tablet: As used in this disclosure, a tablet is a delivery method that comprises an active chemical compound. A tablet may further comprise auxiliary chemical compounds that perform a variety of functions including supplementing the stability and providing additional bulk for the active chemical compound. The tablet form of an active chemical compound and the auxiliary chemical compounds is of a power that is compressed into a single object that is generally taken orally. A tablet is generally formulated to provide a measured dose of the active chemical compound. A tablet is often referred to as a pill.

Twist: As used in this disclosure, to twist means to apply a force to an object such that a first section of the object rotates relative to a second section of the object.

Virus: As used in this disclosure, a virus is a biological entity that is capable of reproduction but does not have the biological mechanisms to generate the energy for replication. A virus "infects" a host cell and uses the biochemical biological processes of the host cell as the energy source that allows the virus to replicate. Because the virus is incapable of independently generating the biochemical energy necessary for reproduction, the traditional view is that viruses are not a form of life. All viruses comprise a nucleic acid structure and a protein shell. The nucleic acid structure is genetic material that is selected from the group consisting of RNA and DNA. The nucleic acid structure is enclosed within the protein shell. The protein shell is known as the capsid. The proteins of the capsid are encoded by the nucleic acid structure. The capsid: a) protects the nucleic acid structure when the virus is dormant; and, b) attaches the virus to a biological structure of a host cell that is suitable to support the replication of the virus. More evolved viruses further comprise an envelope. The envelope is a lipid based structure that is similar to a cell membrane. By similar to the cell membrane is meant that: a) the envelope is formed with a bilayer lipid structure similar to a cell membrane; and, b) the envelope will display membrane protein structures to its environment in a similar to a cell membrane. The envelope encloses the capsid and the nucleic acid structure. In this disclosure, a virus formed with an envelope is referred to as an evolved virus. The term virus can refer to viruses with or without an envelope.

Water: As used in this disclosure, water (CAS 7732-18-5) is a molecule comprising two hydrogen atoms and one oxygen molecule. The phase of water at normal temperature and pressure is liquid. As used in this disclosure, the definition of water is expanded to include dilute water-based solutions of salts and ionic structures using water as the solvent. Water in a gas phase is often referred to as steam. Water in a solid phase is often referred to as ice.

With respect to the above description, it is to be realized that the optimum dimensional relationship for the various components of the invention described above and in FIGS. 1 through 9 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A portable hand-washing kit comprising
a disinfecting structure, a disinfecting compound, and water;
wherein the disinfecting compound is contained in the disinfecting structure;
wherein the water is added to the disinfecting structure;
wherein the portable hand-washing kit is adapted for use with a patient;
wherein the portable hand-washing kit is a portable structure that allows the patient to wash their hands;
wherein the patient washes their hands by inserts their hands into the solution formed by dissolving the disinfecting compound in the water;
wherein the disinfecting compound is a pharmacologically active media that poisons biochemical processes;
wherein the disinfecting structure is a container;
wherein the disinfecting structure is a flexible structure;
wherein the disinfecting structure has an inelastic nature;
wherein the disinfecting structure is a fluid impermeable structure;
wherein the disinfecting structure is a self-standing structure;
wherein the disinfecting structure is a disposable structure;
wherein the disinfecting structure contains a disinfecting solution after the water has been poured into the disinfecting structure;
wherein the flexible structure of the disinfecting structure allows the disinfecting structure to twist into a closed position.

2. The portable hand-washing kit according to claim 1
wherein the disinfecting compound is a chemical compound;
wherein the disinfecting compound is a pharmacologically active media;
wherein the disinfecting compound dissolves to form a disinfecting solution when the water is added to the disinfecting structure;
wherein the disinfecting compound has a structure selected from the group consisting of a tablet structure and a surface coating;
wherein the tablet structure is a compressed structure formed from the disinfecting compound;
wherein the surface coating is a coating formed by the disinfecting compound.

3. The portable hand-washing kit according to claim 2
wherein the disinfecting structure comprises a containment structure, a plurality of access apertures, and a plurality of elastic bands;
wherein the containment structure forms the containment vessel that holds the disinfecting solution formed by the disinfecting compound and the water;
wherein each of the plurality of access apertures is an aperture that is formed through the exterior surface of the containment structure;
wherein a hand of the patient inserts into the containment structure through an access aperture selected from the plurality of access apertures;
wherein each of the plurality of elastic bands is an elastic structure that attaches to an access port selected from the plurality of access apertures;
wherein each of the plurality of access apertures secures its associated access port to the hand of the patient.

4. The portable hand-washing kit according to claim 3
wherein the containment structure is formed from a sheeting;
wherein the containment structure is formed as a bag;
wherein the sheeting that forms the containment structure is formed from a polyurethane;
wherein the containment structure is formed as a flexible structure that is capable of being twisted into a closed position;
wherein the containment structure is formed with enough stiffness that the containment structure forms a self-standing while a patient is washing their hands.

5. The portable hand-washing kit according to claim 4
wherein the plurality of access apertures comprises a first access aperture and a second access aperture;
wherein the first access aperture is an aperture formed through the containment structure;
wherein the first access aperture forms an access port into the interior of the containment structure;
wherein a first hand of the patient inserts into the first access aperture of the containment structure;

wherein the second access aperture is an aperture formed through the containment structure;
wherein the second access aperture forms an access port into the interior of the containment structure;
wherein a second hand of the patient inserts into the second access aperture of the containment structure.

6. The portable hand-washing kit according to claim 5 wherein the plurality of access apertures comprises a first elastic band and a second elastic band;
wherein the first elastic band is an elastic structure;
wherein the first elastic band is a band that attaches to the perimeter of the first access aperture;
wherein the first elastic band seals the first access aperture around the hand of the patient when it is inserted into the containment structure;
wherein the second elastic band is an elastic structure;
wherein the second elastic band is a band that attaches to the perimeter of the second access aperture;
wherein the second elastic band seals the second access aperture around the hand of the patient when it is inserted into the containment structure.

7. The portable hand-washing kit according to claim 6 wherein the disinfecting compound is a chemical compound selected from the group consisting of: a) 2-pyrrolidinone with iodine (CAS 25655-41-8); b) a mixture of 5-chloro-2-(2,4-dichlorophenoxy)-phenol (CAS 3380-34-5) and sodium bicarbonate (CAS 144-55-8); c) a mixture of N-(4-chlorophenyl)-N'-(3,4-dichlorophenyl)-urea (CAS 101-20-2) and sodium bicarbonate (CAS 144-55-8); d) a quaternary ammonium (CAS 8001-54-5); and, e) a sodium 3,5-dichloro-2,4,6-trioxy,1,3,5-triazinaN-1-ide (CAS 2893-78-9);
wherein the 5-chloro-2-(2,4-dichlorophenoxy)-phenol (CAS 3380-34-5) is provisioned as a mixture of 5-chloro-2-(2,4-dichlorophenoxy)-phenol (CAS 3380-34-5) and sodium bicarbonate (CAS 144-55-8);
wherein the sodium bicarbonate (CAS 144-55-8) is added to improve the solubility of the 5-chloro-2-(2,4-dichlorophenoxy)-phenol (CAS 3380-34-5) of the water;
wherein the N-(4-chlorophenyl)-N'-(3,4-dichlorophenyl)-urea (CAS 101-20-2) is provisioned as a mixture of N-(4-chlorophenyl)-N'-(3,4-dichlorophenyl)-urea (CAS 101-20-2) and sodium bicarbonate (CAS 144-55-8).

8. The portable hand-washing kit according to claim 6 wherein the tablet structure is stored within the containment structure.

9. The portable hand-washing kit according to claim 8 wherein the disinfecting compound is 2-pyrrolidinone with iodine (CAS 25655 8;
wherein the 2-pyrrolidinone with iodine (CAS 25655-41-8) is a pharmacologically active media.

10. The portable hand-washing kit according to claim 9 wherein the disinfecting compound is 5-chloro-2-(2,4-dichlorophenoxy)-phenol (CAS 3380-34-5);
wherein the 5-chloro-2-(2,4-dichlorophenoxy)-phenol (CAS 3380-34-5) is a pharmacologically active media;
wherein the 5-chloro-2-(2,4-dichlorophenoxy)-phenol (CAS 3380-34-5) is provisioned as a mixture of 5-chloro-2-(2,4-dichlorophenoxy)-phenol (CAS 3380-34-5) and sodium bicarbonate (CAS 144-55-8);
wherein the sodium bicarbonate (CAS 144-55-8) is added to improve the solubility of the 5-chloro-2-(2,4-dichlorophenoxy)-phenol (CAS 3380-34-5) of the water.

11. The portable hand-washing kit according to claim 10 wherein the disinfecting compound is N-(4-chlorophenyl)-N'-(3,4-dichlorophenyl)-urea (CAS 101-20-2);
wherein the N-(4-chlorophenyl)-N'-(3,4-dichlorophenyl)-urea (CAS 101-20-2) is a pharmacologically active media;
wherein the N-(4-chlorophenyl)-N'-(3,4-dichlorophenyl)-urea (CAS 101-20-2) is provisioned as a mixture of N-(4-chlorophenyl)-N'-(3,4-dichlorophenyl)-urea (CAS 101-20-2) and sodium bicarbonate (CAS 144-55-8).

12. The portable hand-washing kit according to claim 11 wherein the disinfecting compound is quaternary ammonium (CAS 8001-54-5);
wherein the quaternary ammonium (CAS 8001-54-5) is a pharmacologically active media.

13. The portable hand-washing kit according to claim 10 wherein the disinfecting compound is sodium 3,5-dichloro-2,4,6-trioxy,1,3,5-triazinaN-1-ide (CAS 2893-78-9);
wherein the sodium 3,5-dichloro-2,4,6-trioxy,1,3,5-triazinaN-1-ide (CAS 2893-78-9) is a pharmacologically active media.

14. The portable hand-washing kit according to claim 6 wherein the surface coating is applied to the interior surfaces of the containment structure.

15. The portable hand-washing kit according to claim 14 wherein the disinfecting compound is 2-pyrrolidinone with iodine (CAS 25655-41-8);
wherein the 2-pyrrolidinone with iodine (CAS 25655-41-8) is a pharmacologically active media.

16. The portable hand-washing kit according to claim 15 wherein the disinfecting compound is 5-chloro-2-(2,4-dichlorophenoxy)-phenol (CAS 3380-34-5);
wherein the 5-chloro-2-(2,4-dichlorophenoxy)-phenol (CAS 3380-34-5) is a pharmacologically active media;
wherein the 5-chloro-2-(2,4-dichlorophenoxy)-phenol (CAS 3380-34-5) is provisioned as a mixture of 5-chloro-2-(2,4-dichlorophenoxy)-phenol (CAS 3380-34-5) and sodium bicarbonate (CAS 144-55-8);
wherein the sodium bicarbonate (CAS 144-55-8) is added to improve the solubility of the 5-chloro-2-(2,4-dichlorophenoxy)-phenol (CAS 3380-34-5) of the water.

17. The portable hand-washing kit according to claim 16 wherein the disinfecting compound is N-(4-chlorophenyl)-N'-(3,4-dichlorophenyl)-urea (CAS 101-20-2);
wherein the N-(4-chlorophenyl)-N'-(3,4-dichlorophenyl)-urea (CAS 101-20-2) is a pharmacologically active media;
wherein the N-(4-chlorophenyl)-N'-(3,4-dichlorophenyl)-urea (CAS 101-20-2) is provisioned as a mixture of N-(4-chlorophenyl)-N'-(3,4-dichlorophenyl)-urea (CAS 101-20-2) and sodium bicarbonate (CAS 144-55-8).

18. The portable hand-washing kit according to claim 17 wherein the disinfecting compound is quaternary ammonium (CAS 8001-54-5);
wherein the quaternary ammonium (CAS 8001-54-5) is a pharmacologically active media.

19. The portable hand-washing kit according to claim 18 wherein the disinfecting compound is sodium 3,5-dichloro-2,4,6-trioxy,1,3,5-triazinaN-1-ide (CAS 2893-78-9);
wherein the sodium 3,5-dichloro-2,4,6-trioxy,1,3,5-triazinaN-1-ide (CAS 2893-78-9) is a pharmacologically active media.

* * * * *